(12) United States Patent
Wong et al.

(10) Patent No.: US 8,252,312 B1
(45) Date of Patent: Aug. 28, 2012

(54) ORAL SOLID COMPOSITION COMPRISING A LIPID ABSORPTION INHIBITOR

(76) Inventors: David Wong, Milpitas, CA (US); Kate Wensie Wong, Milpitas, CA (US); Spencer Wenyen Wong, Milpitas, CA (US)

( * ) Notice: Subject to any disclaimer, the term of this patent is extended or adjusted under 35 U.S.C. 154(b) by 0 days.

(21) Appl. No.: 13/337,432

(22) Filed: Dec. 27, 2011

(51) Int. Cl.
*A61K 9/28* (2006.01)
*A61K 9/20* (2006.01)
*A61K 31/335* (2006.01)

(52) U.S. Cl. .......... 424/441; 424/400; 424/465; 514/54; 514/56; 514/449; 514/909; 514/338

(58) Field of Classification Search .................... 514/54, 514/449, 909, 56; 424/465, 441, 400
See application file for complete search history.

(56) References Cited

U.S. PATENT DOCUMENTS

| | | | | |
|---|---|---|---|---|
| 4,983,404 A | * | 1/1991 | Raman et al. ..................... 426/3 |
| 5,643,874 A | * | 7/1997 | Bremer et al. ................. 514/4.8 |
| 5,747,464 A | * | 5/1998 | See ................................. 514/26 |
| 5,928,661 A | * | 7/1999 | Fujita et al. .................... 424/402 |
| 6,756,364 B2 | * | 6/2004 | Barbier et al. .................. 514/57 |
| 2005/0238654 A1 | * | 10/2005 | Takeda ..................... 424/195.15 |
| 2008/0248115 A1 | * | 10/2008 | Palepu .......................... 424/474 |
| 2009/0068277 A1 | * | 3/2009 | Park et al. ..................... 424/490 |

OTHER PUBLICATIONS

Goel et al. (Recent patents on drug delivery and formulation 2008, vol. 2, pp. 258-274.*
Niacin info from Mayoclinic 2008 (pp. 1-5), downloaded from the internet on Feb. 22, 2012, URL: http://web.archive.org/web/20081219184027/http://www.mayoclinic.com/health/niacin/CL00036.*
Inotsuka et al. (JP 2005-132801 abstract only.*

* cited by examiner

Primary Examiner — Savitha Rao

(57) ABSTRACT

The present invention provides an oral solid composition comprising a lipase inhibitor, an acid soluble polymer and an excipient. The composition may further comprise a second active. The composition may also further comprise a functional excipient.

3 Claims, No Drawings

ORAL SOLID COMPOSITION COMPRISING A LIPID ABSORPTION INHIBITOR

TECHNICAL FIELD

The present invention is generally in the field of pharmaceutical compositions, and specifically relates to mainly comprising a lipid absorption inhibitor.

BACKGROUND ART

People who are overweight or obese are more likely to develop cardiovascular diseases, diabetes, gallbladder diseases and joint problems. Carrying extra weight implies carrying extra risks for certain types of cancers including endometrial, breast, prostate and colon cancers. One way to control weight gain, glucose level or lipid level is to take medications or supplements capable to prevent a fast absorption of glucose and lipid. A composition comprising a lipid absorption inhibitor and further a glucosidase inhibitor may achieve such objectives.

Glucosidase inhibitor or lipid absorption inhibitor has been suggested to use as a secondary drug in compositions, such as US Patent Applications 20060135460, 20060287242 and 20080242593. Current invention discloses various compositions comprising a lipid absorption inhibitor and further a glucosidase inhibitor.

Popular lipid absorption inhibitors are ezetimibe and orlistat. Ezetimibe localizes at the brush border of the small intestine and inhibits the absorption of cholesterol, leading to a decrease in the delivery of intestinal cholesterol to the liver. This causes a reduction of hepatic cholesterol stores and an increase in clearance of cholesterol from the blood. Orlistat is in a class of medications called lipase inhibitors. Other lipid absorption inhibitors are SCH48461, SCH58235, SCH 58053, rexinoids, saponins (such as pamaqueside and tiqueside).

Glucosidase inhibitors slow the digestion of starch in the small intestine, so that glucose from the starch of a meal enters the bloodstream more slowly. Examples of inhibitors are miglitol, acarbose, aspergillusol A, (Z)-3-butylidenephthalide (isolated from *Ligusticum port*), butyl-isobutyl-phthalate (isolated from *Laminaria japonica* rhizoid), copper sulfate, difluorotetrahydropyridothiazinone, dieckol (isolated from *Ecklonia*), duboscic acid, ganoderol B (isolated from *Ganoderma lucidum*), hydroxycoumarin derivatives, kaempferol, kaempferol-3-O-rutinoside, kotalanol, methylelaiophylin (isolated from *Streptomyces melanosporofaciens*), (E)-1-phenyl-3-(4-styrylphenyl)urea derivatives, N-(phenoxydecyl)phthalimide derivatives, polyhydroxybenzophenones, pycnalin (isolated from *Acer pycnanthum*), quercetin, Salacinol derivatives (from *Salacia reticulate*), voglibose, and extracts of cinnamon, *Nymphaea stellata* flowers, *Phellinus merrillii, Schizandra chinensis*, white bean (*Phaseolus vulgaris*) extracts.

The composition further comprises rosin gum, niacin, statin, sweetener or their combinations. Some compositions may also comprise polyethylene oxide.

OBJECTS OF THE INVENTION

In the invention, a lipid absorption inhibitor is incorporated into a solid dosage form. A second active, or a functional excipient such as an acid-soluble polymer, sweetener, polyethylene oxide, and other excipients, such as filler, binder, disintegrant, lubricant, suspending agent, wetting agent, glidant, are also present in the composition. The object of this invention is to prepare simple oral solid compositions essentially comprising a lipid absorption inhibitor, an functional excipient and one or more other excipients.

SUMMARY OF THE INVENTION

The present invention provides an oral solid composition of a drug and methods of manufacture that render a composition mainly consisting of a lipid absorption inhibitor, an acid-soluble polymer and a pharmaceutical acceptable excipient. The composition is optionally film-coated. The composition may further comprise polyethylene oxide, sweetener, a natural gum and a second active.

The composition can be in the form of pellets, beads, granules and tablets. Common pharmaceutical manufacturing methods such as pelletization, granulation, compression can be used to prepare the composition.

DETAILED DESCRIPTION

The present invention provides an oral solid composition and methods for preparing such compositions. The oral solid compositions are in the form of tablets or capsules and may have one or more of the following characteristics: (1) comprising a lipid absorption inhibitor, a pharmaceutical acceptable excipient, a functional excipient and/or a second active; (2) providing fast or slow release; (3) are in the form of tablet; and (4) optionally coated for appearance, tasking masking, extended-release or delayed-release.

According, in one aspect this invention provides an oral solid composition comprising a lipid absorption inhibitor, an acid-soluble polymer, and a pharmaceutical acceptable excipient, wherein the lipid absorption inhibitor is a lipase inhibitor, e.g. orlistat, wherein the acid-soluble polymer is a synthetic polymer with an amino group. The preferred synthetic polymer with an amino group is amino methacrylate copolymer. The composition may further comprise a second active or a functional excipient or a combination thereof, wherein the second active is selected from a group consisting of alpha-glucosidase inhibitors, statins, phytochemicals, plant extracts and vitamins, and wherein the functional excipient is selected from a group consisting of a sweetener, a natural gum and eutectic formers. The preferred eutectic formers are menthol and camphor. The preferred natural gum is a natural gum containing abietic acid, e.g. rosin gum. The preferred alpha-glucosidase inhibitor is acarbose, and the preferred phytochemical is beta-sitosterol. The composition is the form of a tablet, preferably a chewable tablet.

In another aspect, the invention provides an oral solid composition comprising a lipase inhibitor, acarbose, a synthetic acid-soluble polymer, and an acceptable pharmaceutical excipient, wherein the preferred lipase inhibitor is orlistat. The composition may further comprise a functional excipient, and wherein the functional excipient is selected from a group consisting of a sweetener, a natural gum, a non-polysaccharide polymer, eutectic formers or a combination thereof. The preferred synthetic acid-soluble polymer is amino methacrylate copolymer. The preferred natural gum is a natural gum containing abietic acid, e.g. rosin gum, the sweetener is selected from a group consisting of aspartame and Stevia extracts, and the non-polysaccharide polymer is polyethylene oxide. The composition may contain a disintegrant and is in the form of an oral tablet or a chewable tablet.

In a further aspect, the invention provides an oral solid composition comprising a lipase inhibitor, a synthetic acid-soluble polymer, a second active and an excipient, wherein the synthetic acid-soluble polymer is amino-methacrylate copolymer, wherein the lipase inhibitor is orlistat, and wherein the second active is selected from a group consisting of Schizandra extract and kaempferol-3-O-rutinoside. The composition is in the form of a chewable tablet. The composition may further comprise a natural gum containing abietic acid, wherein the natural gum is rosin gum. The composition may also further comprise a vitamin, wherein the vitamin is niacin. The composition may further comprise a sweetener, such as aspartame and stevia extract.

In one aspect, the invention provides an oral solid composition comprising a lipase inhibitor, a synthetic acid-soluble polymer, a second active and an excipient, wherein the synthetic acid-soluble polymer is amino-methacrylate co-polymer, wherein the lipase inhibitor is orlistat, and wherein the second active is selected from a group consisting of ezitimibe, *Phaseolus vulgaris* extract, rexinoids, saponins, statins and vitamins. The composition is in the form of a chewable tablet. The composition may further comprise a natural gum containing abietic acid, wherein the natural gum is rosin gum. The product label instructs users to chew the tablets. And, the product label may further request the users to swallow the "chewed" tablet.

In all compositions, the excipient is a disintegrant, a lubricant, a filler, a binder, or a combination thereof. The composition is optionally film-coated.

Pharmaceutical composition according to the present invention can be obtained by pelletization, drug-layering on inert bead, granulation (wet granulation and roller-compaction), slugging and compression. The composition is optionally film-coated.

The active pellet can be prepared from powders comprising the actives and excipients by direct pelletization, using state of the art pharmaceutical equipment for pelletization such as, for example, but not limited to, extruders and spheronizators, rotor fluid bed equipment, high shear mixers designed for spheronization of obtained agglomerates. The products of said process are matrix pellets, wherein the actives are preferably homogeneously distributed in the pellet body. In one embodiment of the present invention the active core of the present invention can be produced for example by hot melt techniques such as melt pelletization in high shear mixers, by melt extrusion with optional subsequent spheronization, by melt granulation or similar processes. The obtained active cores can be further coated by plurality of film coatings.

The active granule can be produced by state of the art processes, e.g. wet granulation, melt-granulation, roller-compaction or melt granulation.

The active tablet can be produced by state of the art processes such as for example, but not limited to, direct compression of the actives and denaturant in admixture with other excipient(s), compression of a pre-granulated mixture of the actives, denaturant and other excipient(s) selected from the group consisting of, but not limited to, binders, fillers, disintegrants, lubricants, and glidants.

The active-layered bead can be formed by applying a layer containing actives and denaturant to an inert bead. A convenient manner of coating the bead with actives can be the powder layering process which is performed using state of the art functional equipment such as for example, but not limited to, rotor tangential fluid bed systems, non-perforated pan coaters, rotating plate equipment or bottom spray fluid bed systems, where rotor tangential fluid bed systems such as Glatt Gmb H and rotating plate equipment such as Freud CF-Granulator, produced by Vector Corp. are preferred. The inert beads are moistened with a solution of binder, and then the actives together with other excipients are added as a powder and the layered pellets are dried in the same equipment as the coating is performed or other specialized equipment for drying, such as a drying chamber with or without vacuum.

Alternatively, the layer with actives can be formed in the conventional layering process, performed in state of the art fluid bed equipment such as for example, but not limited to, bottom spray systems, such as for example obtainable by Glatt GmbH, Niro Pharma systems, top or tangential spray systems, or classical nonperforated pan coaters. Actives dispersed together with at least one acceptable excipient in a suitable liquid. The layering-process is performed by spraying the liquid onto inert beads in a fluid-bed.

All steps of coating i.e. coating and drying of pellets with individual layers are preferably performed is the same equipment. Tablet coating is preferably performed with a pan-coater or a fluid-bed.

The terms drugs, therapeutics, actives and biological actives are inter-changeable.

"Optional" or "optionally" means that the subsequently described circumstance may or may not occur, so that the description includes instances where the circumstance occurs and instances where it does not.

Singular forms included in the claims such as "a", "an" and "the" include the plural reference unless expressly stated or the context clearly indicates otherwise.

By "pharmaceutically acceptable" is meant a carrier comprised of a material that is not biologically or otherwise undesirable.

In this application, the functional excipients are sweetener, natural gum and acid-soluble polymer. Natural gum containing abietic acid, such as rosin gum, is preferred. Examples of the acid-soluble polymer include chitosan and EUDRAGIT® E PO (amino-methacrylate co-polymer). Examples of sweeteners are aspartame, stevia extracts and other sugar substitutes.

The alpha-glucosidase inhibitor is selected from a group of miglitol, acarbose, aspergillusol A, (Z)-3-butylidenephthalide, butyl-isobutyl-phthalate, copper sulfate, difluorotetrahydropyridothiazinone, dieckol, duboscic acid, ganoderol B, hydroxycoumarin derivatives, kaempferol, kaempferol-3-O-rutinoside, kotalanol, methylelaiophylin, (E)-1-phenyl-3-(4-styrylphenyl)urea derivatives, N-(phenoxydecyl)phthalimide derivatives, polyhydroxybenzophenones, pycnalin, quercetin, Salacinol derivatives, voglibose, and extracts of cinnamon, *Nymphaea stellata* flowers, *Phellinus merrillii*, *Schizandra chinensis*, and white bean.

The lipid absorption inhibitor is selected from a group consisting of ezetimibe, orlistat, rexinoids, chitin, chitosan and saponins. Other examples include SCH48461, SCH58235, SCH 58053 and other lipid absorption inhibitors under development. Orlistat is in a class of medications called lipase inhibitors.

The sweetener is selected from a group consisting of stevia extract, aspartame and other popular sugar substitutes.

The pharmaceutical acceptable excipients are selected from a group of fillers, diluents, disintegrants, binders, extended-release aids, glidants and lubricants alone or in any combination. The compressed tablet is optionally coated with an immediate-disintegrating film for appearance and task-masking purposes, an enteric polymeric film for delayed drug release purpose or an water-insoluble film for extended-release purpose.

The amount of pharmaceutically acceptable excipients employed will depend upon how much active agent is to be used. One excipient can perform multi-functionally.

Binders include, but are not limited to, starches such as potato starch, wheat starch, corn starch; microcrystalline cellulose; celluloses such as hydroxypropyl cellulose, hydroxyethyl cellulose, hydroxypropyl methylcellulose, ethyl cellulose, sodium carboxy methylcellulose; natural gums like acacia, alginic acid, guar gum; liquid glucose, dextrin, povidone, syrup, polyethylene oxide, polyvinyl pyrrolidone, poly-N-vinyl amide, polyethylene glycol, gelatin, poly propylene glycol, tragacanth, combinations thereof and other materials known to one of ordinary skill in the art and mixtures thereof.

Fillers or diluents, which include, but are not limited to sugar, dextrates, dextrin, dextrose, fructose, lactitol, mannitol, sucrose, starch, lactose, xylitol, sorbitol, talc, microcrystalline cellulose, calcium carbonate, calcium phosphate dibasic or tribasic, calcium sulphate, and the like can be used.

Lubricants may be selected from, but are not limited to, those conventionally known in the art such as magnesium, aluminum or calcium or zinc stearate, polyethylene glycol, glyceryl behenate, mineral oil, sodium stearyl fumarate, stearic acid, hydrogenated vegetable oil and talc.

Glidants include, but are not limited to, silicon dioxide; magnesium trisilicate, powdered cellulose, starch, talc and tribasic calcium phosphate, calcium silicate, magnesium silicate, colloidal silicon dioxide, silicon hydrogel and other materials known to one of ordinary skill in the art.

The pharmaceutical dosage form of the invention can optionally have one or more coatings such as moisture-barrier film coating, sugar coating and other coatings known in the art.

These coating layers comprises one or more excipients selected from the group comprising coating agents, plasticizers, channeling agents, opacifiers, taste-masking agents, fillers, polishing agents, coloring agents, anti-tacking agents and the like.

Coating agents which are useful in the coating process, include, but are not limited to, polysaccharides such as maltodextrin, alkyl celluloses such as methyl or ethyl cellulose, cellulose acetate, hydroxyalkylcelluloses (e.g. hydroxypropylcellulose or hydroxypropylmethylcelluloses); polyvinylpyrrolidone, acacia, corn, sucrose, gelatin, shellac, cellulose acetate phthalate, lipids, synthetic resins, acrylic polymers, OPADRY® coating systems, polyvinyl alcohol (PVA), copolymers of vinylpyrrolidone and vinyl acetate (e.g. marketed under the brand name of PLASDONE®) and polymers based on methacrylic acid such as those marketed under the brand name of EUDRAGIT®. These may be applied from aqueous or non-aqueous systems or combinations of aqueous and non-aqueous systems as appropriate.

Additives can be included along with the film formers to obtain satisfactory films. These additives can include plasticizers such as dibutyl phthalate, triethyl citrate, polyethylene glycol (PEG) and the like, channeling agents such as surfactants, short-chain water-soluble polymers, salts and the like, antitacking agents such as talc, stearic acid, magnesium stearate and colloidal silicon dioxide and the like, fillers such as talc, precipitated calcium carbonate, polishing agents such as Beeswax, carnauba wax, synthetic chlorinated wax and opacifying agents such as titanium dioxide and the like. All these excipients can be used at levels well known to the persons skilled in the art.

EXAMPLES OF INVENTION

The foregoing examples are illustrative embodiments of the invention and are merely exemplary. A person skilled in the art may make variations and modifications without deviating from the spirit and scope of the invention. All such modifications and variations are intended to be included within the scope of the invention.

Example 1

Alpha-glucosidase inhibitor, 10% and lipid absorption inhibitor 20% are blended with rosin gum, 10%, polyethylene oxide, 10%, microcrystalline cellulose, 46%, sodium lauryl sulfate 2%, an acid-soluble polymer 1% and magnesium stearate, 1%, and then compressed into tablets.

Example 2

Polyethylene oxide, 34 g, and an acid-soluble polymer 1 g mixed with glycerol monostearate, 3 g, an alpha-glucosidase inhibitor, 30 g and orlistat, 30 g, granulated with water, passed through a screen, dried at about 55 deg. C. and grinded into small particles. Rosin gum is passed through a screen. The granule is mixed with the screened gum, fillers and lubricants, and then compressed into tablets.

Example 3

A alpha-glucosidase inhibitor, 7.11 g and a lipid absorption inhibitor, 7.11 g are blended with polyethylene oxide, 25.3 g, citric acid or sodium lauryl sulfate, 1 g, an acid soluble polymer, 6.59 g and glycerol monostearate, 0.88 g, compressed into tablets.

Example 4

Orlistat 250 mg, cinnamon extract 300 mg, polyethylene oxide 50 mg and KOLLIDON SR® (Polyvinyl Acetate:Polyvinyl Pyrolidone, 8:2) are sifted through s. s sieve of mesh 30 and blended together. The blend was lubricated with an acid soluble polymer, sodium lauryl sulfate, rosin gum, colloidal silicon dioxide and talc and the lubricated blend is compressed into tablets.

Example 5

Orlistat 10 mg, *Schizandra chinensis* extract 300 mg, microcrystalline cellulose 200 mg, polyethylene oxide 50 mg and KOLLIDON SR® (Polyvinyl Acetate:Polyvinyl Pyrolidone, 8:2) are sifted through s. s sieve of mesh 30 and blended together. The blend was lubricated with sodium lauryl sulfate, an acid soluble polymer, rosin gum, colloidal silicon dioxide and talc and the lubricated blend is compressed into tablets.

Example 6

Rexinoid 50 mg, *Phellinus merrillii* extract 300 mg, an acid soluble polymer 10 mg, rosin gum 10 mg and polyethylene oxide are sifted through s. s. sieve of mesh 40 and blended together. The blend is granulated using nonaqueous granulation using hydroxypropyl cellulose as the binder. The granulated mass is dried at 45.degree. C. The dried granules were sized through a sieve of mesh 20 and the granules are lubricated with sodium lauryl sulfate, talc and colloidal silicon dioxide. The lubricated blend is encapsulated or compressed into tablets.

Example 7

*Schizandra chinensis* extract 250 mg, orlistat 30 mg, an acid soluble polymer 10 mg, rosin gum 10 mg and polyethylene oxide are sifted through s. s. sieve of mesh 40 and blended together. The blend is granulated using nonaqueous granulation using hydroxypropyl cellulose as the binder. The granulated mass is dried at 45.degree. C. The dried granules were sized through s. s. sieve of mesh 20 and the granules are lubricated with sodium lauryl sulfate, talc and colloidal silicon dioxide. The lubricated blend is encapsulated or compressed into tablets.

We claim:

1. An oral solid composition comprising a lipase inhibitor, an acid soluble polymer and an excipient, wherein the lipase inhibitor is orlistat, wherein the acid soluble polymer is an amino methacrylate copolymer, wherein oral solid composition is a chewable tablet, wherein the composition further comprises a natural gum containing abietic acid, and wherein the natural gum is rosin gum.

2. An oral solid composition comprising an acid-soluble polymer, acarbose, a lipase inhibitor and an acceptable pharmaceutical excipient, wherein the acid-soluble polymer has an amino group, wherein the lipase inhibitor is orlistat, wherein the oral solid composition is a chewable tablet, wherein the acid-soluble polymer is an amino methacrylate copolymer, and wherein the oral solid composition further comprises a natural gum containing abietic acid.

3. An oral solid composition comprising a lipase inhibitor, an excipient, an acid soluble polymer and a secondary active selected from a group consisting of Schizandra extract and kaempferol-3-O-rutinoside, wherein the lipase inhibitor is orlistat and wherein the acid-soluble polymer is amino methacrylate copolymer, wherein the oral solid composition is a chewable tablet, and wherein the solid composition further comprises a natural gum, wherein the natural gum contains abietic acid.

* * * * *